United States Patent [19]

Kalyon et al.

[11] Patent Number: 5,277,058
[45] Date of Patent: Jan. 11, 1994

[54] ADJUSTABLE GAP RHEOMETER

[76] Inventors: Dilhan M. Kalyon, 529 N. St., Teaneck, 07666; Halit S. Gokturk, 209 Second St., Apt. 2R, Hoboken, both of N.J. 07030

[21] Appl. No.: 979,747

[22] Filed: Nov. 23, 1992

[51] Int. Cl.$^5$ .............................. G01N 11/04
[52] U.S. Cl. .................. 73/54.11; 73/54.14
[58] Field of Search ............ 73/54.11, 54.14; 33/813, 823, 828, 824, 825, 826; 269/86, 119, 140, 216, 320

[56] References Cited

U.S. PATENT DOCUMENTS

| | | | |
|---|---|---|---|
| 1,554,899 | 9/1925 | Vick | 269/86 |
| 1,850,178 | 3/1932 | McChesney | 269/140 |
| 2,661,540 | 12/1953 | Dulligan | 33/544.5 |
| 2,835,040 | 5/1958 | D'Elia | 33/813 |
| 3,046,666 | 7/1962 | Mesich | 33/813 |
| 3,203,225 | 8/1965 | Sieglaff et al. | 73/54.14 |
| 3,270,553 | 9/1966 | Ballman et al. | 73/54.14 |
| 3,595,305 | 7/1971 | Welty et al. | 73/54.11 |
| 4,313,339 | 2/1982 | Nichols et al. | 73/54.14 |
| 4,335,516 | 6/1982 | Edelstein | 33/813 |
| 4,448,736 | 5/1984 | Emery et al. | 425/145 |
| 4,466,274 | 8/1984 | Starr, Jr. | 73/54.01 |
| 4,587,837 | 5/1986 | Newbould | 73/54.04 |
| 4,817,416 | 4/1989 | Blanch et al. | 73/54.04 |

OTHER PUBLICATIONS

Chang Dae Han, "Measurement of the Rheologial Properties of Polymer Melts with Slit Rheometer", Journal of Applied Polymer Science, vol. 15, pp. 2567-2577 (1971).

Paul W. Springer, Robert S. Brokey and R. Emerson Lynn, "Development of an Extrusion Rheometer Suitable for On-Line Rheological Measurements", Polymer Engineering and Science, vol. 15, No. 8, pp. 583-587 (Aug. 1975).

Primary Examiner—Robert J. Warden
Assistant Examiner—Theresa A. Trembley
Attorney, Agent, or Firm—Pennie & Edmonds

[57] ABSTRACT

An improved rheometer of the present invention includes an adjustable gap through which a flowing system is forced. The inner cavity dimension of the gap is variable so as to give a user of the rheometer an ability to vary the separation gap and the length over diameter ratio. This, in turn, allows the user to determine the shear rate and shear stress along the wall of the cavity for varying deformation rates. Thus, the shear viscosity of the flowing system can be characterized for non-Newtonian systems without varying the volumetric flow rate. One of the preferred embodiments of the adjustable gap rheometer is a slit rheometer in which the flowing system is forced through a slit having generally more length than width and more width than gap. The slit rheometer is made adjustable by holding the body of the rheometer stationary while moving an adjustable wall which forms one of the sides of the slit. Another preferred embodiment of the adjustable gap rheometer includes two concentric portions comprising a mandrel portion and a bushing portion. Axial movement of one of the portions relative to the other varies the separation between the components.

18 Claims, 2 Drawing Sheets

ADJUSTABLE GAP RHEOMETER

BACKGROUND OF THE INVENTION

This invention relates to the characterization of a flowing system such as a fluid or a mixture of fluids or a mixture of liquids with gases and/or solids by determining the rheological properties of the flowing system. More particularly, the invention relates to an improved rheometer having an adjustable inner cavity dimension so that properties of the flowing system are easily varied and the flowing system can be characterized without altering the volumetric flow rate of the flowing system.

Generally, rheometers operate by forcing the flowing system to be characterized through a die at a constant volumetric flow rate and determining specific properties of the flowing system such as the shear rate and shear stress of the flowing system at the wall of the die in order to determine the shear viscosity. These properties are characteristic of the flow and deformation behavior of the flowing system. The shear viscosity, in particular, is the most important rheological property.

The flow and deformation behavior are related to primary characteristics of the flowing system such as molecular weight, molecular weight distribution, extent of chain branching in polymer melts, degree of cure or conversion in a reacting system, and various microstructural distributions in multiphase systems. The microstructural distributions include the size distributions, locations and orientations of solid components in the flow, the concentration, shape, surface and size distributions of liquid droplets and the content and size distributions of gaseous components. Thus, characterization of the rheological behavior of a flowing system provides information on the structure of the system.

The rheological properties of the flowing system are characterized by employing material functions such as wall shear stress versus deformation rate at the wall or shear viscosity versus deformation rate determined on the basis of well-defined steady flows.

Rheometers of the prior art include capillary or slit rheometers. They operate by forcing the flowing system through a capillary die or a slit die at a specified volumetric flow rate with a drive mechanism such as a piston or a gear mechanism.

Because shear viscosity of a non-Newtonian flowing system is dependent on the deformation rate of the system, characterization of a non-Newtonian flowing system requires that shear rate and shear stress values be determined at multiple deformation rates to determine the viscosity over the deformation range of interest. Conventional rheometers achieve this by altering the volumetric flow rate into the rheometer. In this way, properties of the flowing system such as the shear rate and shear stress values are altered, and it is possible to determine the viscosity of the particular flowing system of interest over the deformation range of interest. However, altering the flow rate can change the structure and, hence, the rheological properties of the flowing system if a continuous process is used to deliver the flowing system to the rheometer. This distorts the results of the rheological study. Further, generating multiple flow rates requires equipment which is both cumbersome and expensive. Thus, a need exists for a rheometer which can determine the shear viscosity of non-Newtonian flowing systems from a constant flow rate through the rheometer.

SUMMARY OF THE INVENTION

An improved rheometer of the present invention includes an adjustable gap through which the flowing system is forced. The inner cavity dimension of the gap is variable so as to give a user of the rheometer an ability to vary the separation gap and the length over diameter ratio. This, in turn, allows the user to measure the shear rate and shear stress along the wall of the cavity for varying deformation rates. Thus, the shear viscosity of the flowing system can be determined for non-Newtonian systems without varying the volumetric flow rate.

One of the preferred embodiments of the adjustable gap rheometer is a slit rheometer. The slit rheometer comprises a gap through which the flowing system is forced which is shaped as a slit having generally more length than width and more width than gap. The slit rheometer is made adjustable by holding the body of the rheometer stationary while moving an adjustable wall which forms one of the sides of the slit. In this method, the gap dimension is made variable.

Another preferred embodiment of the adjustable gap rheometer includes two concentric portions comprising a mandrel portion and a bushing portion. Axial movement of one of the portions relative to the other varies the separation between the components. Thus, the gap between these portions through which the flowing system flows can be altered to create varying deformation rates of the flowing system, and the viscosity can be measured from measuring the shear stress of the flowing system for each deformation rate.

The advantages of the adjustable gap rheometer are many. First, the volumetric flow rate of the flowing system is maintained at a constant rate, thus eliminating the cost of expensive equipment required to alter the flow rate. Even more importantly, the constant flow rate maintains the microstructure of flowing systems that are sensitive to the thermo-mechanical history to which they are exposed during processing (especially multi-phase flowing systems) before they arrive at the separation gap of the rheometer. Thus, the rheological behavior of the flowing system is maintained during pre-gap processing, and the shear viscosity of the flowing system is measured with greater accuracy.

Another advantage of the adjustable gap rheometer is the ability to "structure" the material that flows through it by altering the deformation rates imposed on the flowing systems. Structuring the flowing material comprises altering the microstructural distributions of the components of the flowing system. The deformation rate imposed on the flowing system created by the particular gap through which the system flows alters the distribution of system components and hence, alters the microstructural distribution. Thus, by sending the flowing system through the adjustable gap rheometer, various microstructural features of the system can be determined for a particular flowing system. These features can be characterized by techniques such as computer aided tomography, magnetic resonance imaging, acoustic emission techniques, infrared imaging, and others. These microstructural features of the flowing system can later be used to create better flowing systems with improved microstructure, and, hence, better ultimate properties, to better understand the particular flowing system, or to help design better experiments which can accommodate for the new microstructure distribution so as to more accurately characterize the rheological properties of the flowing system.

An additional advantage includes the ease with which the rheometer can be adjusted (as opposed to prior art techniques requiring a complete replacement or adjustment of the die upon stopping, and removal of the die of the rheometer at great expense and effort).

BRIEF DESCRIPTION OF THE FIGURES

These and other objects, features, elements and advantages of the invention will be more readily apparent from the following description of the invention in which.

DETAILED DESCRIPTION OF THE PREFERRED EMBODIMENT

A slit rheometer measures viscosity of a flowing system by measuring the apparent flowing system shear rate ($\gamma$) as defined by $$\gamma = \frac{6Q}{WH^2}$$

where Q is the volumetric flow rate, W is the width of the slit, and H is the separation gap of the slit; and the shear stress ($\tau_w$) of the flowing system at the wall of the slit as defined by $$\tau_w = \frac{H \Delta P}{2L}$$

where L is the slit length over which the shear stress is measured, and $\Delta P$ is the pressure drop over the slit length of the fully developed flow. Known corrections which are dependent on the wall shear stress versus apparent shear rate behavior of the flowing system are applied to the apparent shear rate to determine true shear rate at the wall, $\gamma_w$. Shear viscosity ($\eta$) is defined by $$\eta = \frac{\tau_w}{\gamma_w}.$$

To determine the shear viscosity of a non-Newtonian fluid (i.e., a fluid wherein the shear viscosity is dependent on the deformation rate), the shear viscosity values must be determined at multiple deformation rates.

To alter the deformation rate of the flowing system, the separation gap, H, of the rheometer is altered. Thus, with a constant flow rate, Q, the shear viscosity, $\eta$, of the flowing system can be determined. The rheometer of the invention can characterize the complete rheological behavior of the flowing system over a broad range of deformation rates, typically 0.01 to 5,000 s$^{-1}$.

Figure 1:
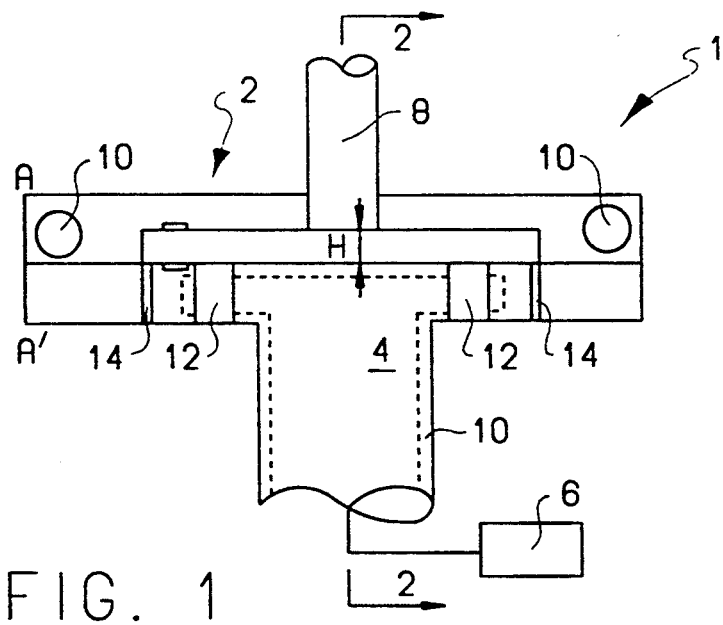
FIG. 1 is a diagrammatic representation of one embodiment of an adjustable gap rheometer.
Figure 2:
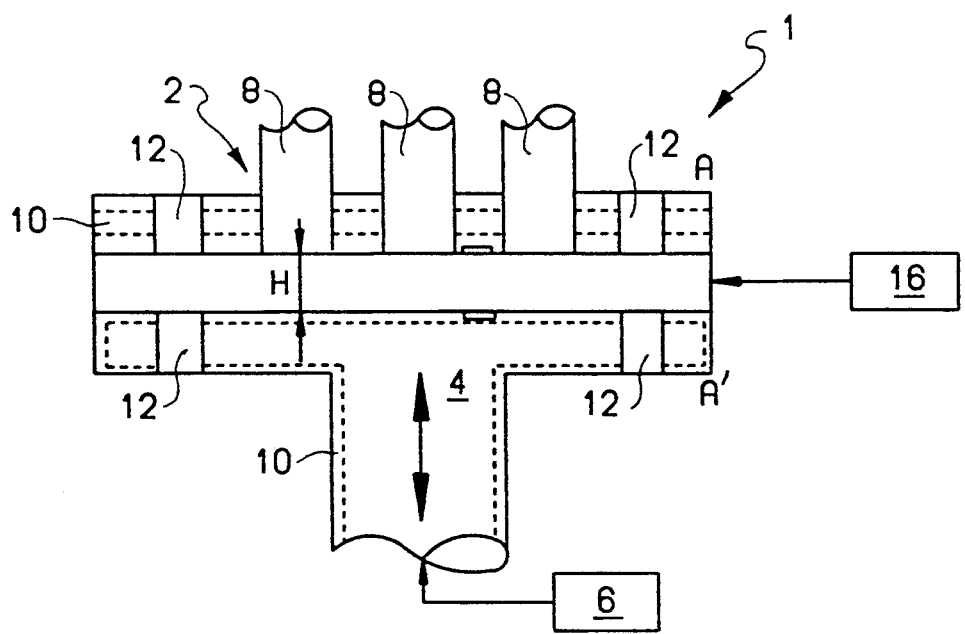
FIG. 2 is a cross-sectional view of the embodiment of the adjustable gap rheometer depicted in FIG. 1 taken at Section line 2—2.

FIGS. 1 and 2 depict an embodiment of an adjustable gap rheometer of the invention comprising a slit die rheometer. The rheometer 1 comprises a stationary section 2 and a moveable section 4 which form the rheometer slit therebetween. In the alternative, the stationary and moveable sections can be reversed to achieve the same result. The moveable section has two-directional vertical movement and is driven by a stepper motor 6 or by other such mechanisms. Movement of the moveable section 4 increases or decreases the separation gap, H, of the rheometer, thus varying the deformation rate of the flowing system.

The rheometer includes a plurality of flow property measuring devices 8 such as pressure transducers, shear stress transducers, optical windows and temperature thermocouples. Heating/cooling circulation channels 10 through which heat transfer fluids can be circulated at a desired temperature and rate maintain a constant temperature in the system. Cartridge type heaters 12 are also provided for better temperature control. Gasket elements 14 positioned adjacent the moveable section 4 prevent the fluid from leaking out of the slit. These gasket elements can comprise a sealing material such as a teflon material to create a strong seal.

The flowing system to be tested is forced through the rheometer at a constant flow rate, Q, which is generated by a continuous processor 16 such as a single or twin screw extruder or kneader which is run at the starved mode. The processor is externally controlled by feeding it at a constant flow rate. Alternatively, the flow rate could be generated by a gear pump installed in-line to feed the flowing system at a constant flow rate.

The constant volumetric flow rate is essential to maintain a constant processing history of the flow, which, in turn, maintains a constant microstructural distribution in the flowing system prior to entry into the separation gap. The microstructural distribution in the flow will determine the response of the flowing system to a deformation rate, and will, therefore, affect the accurate characterization of the rheological properties of the flowing system. Thus, the ability to run the rheometer at a constant flow rate will produce a more accurate determination of the shear viscosity.

Figure 3:
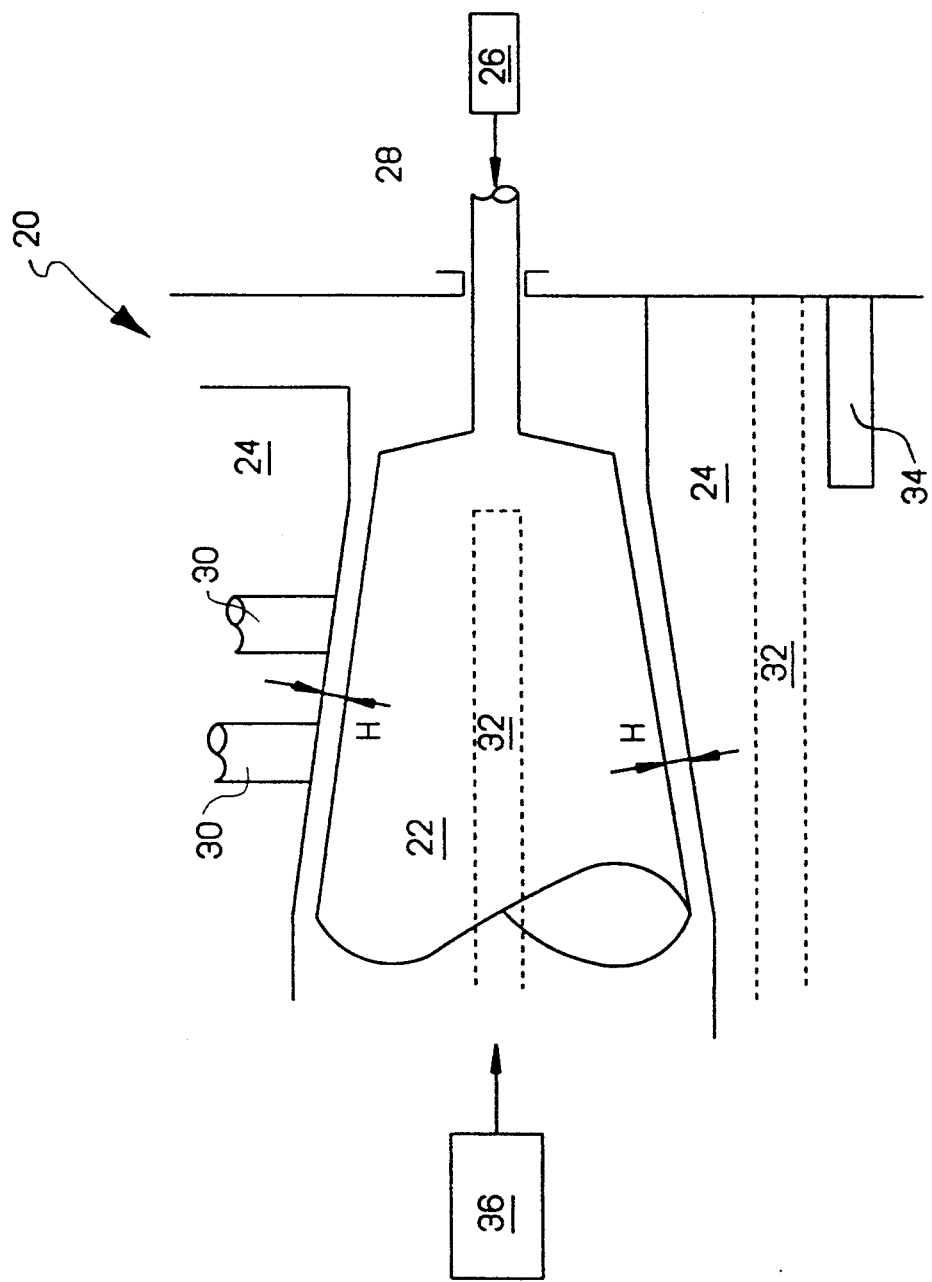
FIG. 3 is a diagrammatic view of another embodiment of an adjustable gap rheometer.

Another embodiment of the invention is depicted in FIG. 3. The rheometer 20 comprises a concentric arrangement of a mandrel 22 and bushing 24. The structure 20 comprises a mandrel 22 which is tapered at a specific incline angle (for example 8°), which is moveable within a die bushing 24, which can be tapered at a generally larger angle than the mandrel (for example 9°). Alternatively, the mandrel taper angle and bushing taper angle could be the same. The taper angles may be maintained at less than 10° to preserve the simplified flow field which allows for better characterization of rheological properties. Between the mandrel 22 and the bushing 24 is a separation gap, H, through which a flowing system is forced in order to determine its rheological properties. Stepper motor 26, is coupled to the mandrel 22 via a rod or screw 28 to provide two-directional linear displacement of the mandrel. This, in turn, increases or decreases the separation gap, H, between the mandrel 22 and bushing 24 by an amount which is a function of the difference between the taper angles of the mandrel and the bushing, and the linear displacement of the mandrel within the bushing.

As in the case of the embodiment of FIG. 1, changing the separation gap, H, of the rheometer of FIG. 3 will change the wall deformation rate of the flowing system and thus will allow for the calculation of the shear viscosity of a non-Newtonian fluid. The rheometer includes a plurality of flow property measuring devices including pressure transducers, shear stress transducers, temperature thermocouples and optical windows, all diagrammatically illustrated as elements 30, which measure flowing system properties necessary for calculating the rheological properties of the flowing system. A heat transfer device comprising heating/cooling circulation channels 32 maintains a constant temperature in the rheometer. Further, heating cartridges 34 can be added to provide better temperature control.

The flowing system is delivered to the rheometer sufficiently pressurized and at a constant volumetric flow rate. The volumetric flow rate is maintained at a constant value through the use of device 36 which comprises either a starve fed continuous processor or a constant volumetric delivery device such as a gear pump. As described above, maintaining a constant volumetric flow rate through the rheometer permits accurate determinations of the deformation rate, which will, in turn, result in more accurate determinations of the shear viscosity of the flowing system.

Again, as above, the material functions of a flow system must be determined to characterize the rheological behavior of the system. The material functions of a particular flowing system are dependent upon the geometry of the separation gap of the rheometer. Because the geometry of the mandrel-bushing embodiment of the adjustable gap rheometer is different from the geometry of the slit rheometer, the equations used to determine the apparent flowing system shear rate ($\gamma$), the true shear rate at the wall $\gamma_w$, the shear stress of the flowing system at the wall of the gap ($\tau_w$), and, consequently, the shear viscosity ($\eta = \tau_w/\gamma_w$) in a mandrel-bushing type of rheometer are different from those used in the slit rheometer (described above). However, the equations which describe the flow of the mandrel-bushing embodiment are well known in the art.

Otherwise, the rheometer functions as described with respect to the embodiment depicted in FIGS. 1 and 2. Briefly, the flowing system is forced through separation gap, H, which allows for a determination of the deformation rate at the wall. The shear stress at the wall and the shear rate at the wall are calculated, and the shear viscosity value is determined therefrom for this deformation rate.

Both embodiments described above can be utilized to "structure" the flow system. Structuring the flow system comprises altering the microstructural distribution of the flow. In this rheometer, this is accomplished by changing the separation gap of the rheometer which alters the deformation rate imposed on the flowing systems. These microstructural distributions can be initially determined by computer aided tomography, magnetic resonance imaging, acoustic emission techniques, infrared imaging, and others. After initial determination, the microstructure will be known for various deformation rates of the flowing system. It can then be used to better understand the flowing system, to help create new and improved flowing systems having improved microstructures, or to design better rheological experiments which accommodate for the new microstructure distribution so as to more accurately characterize the rheological properties of the particular flowing system.

While it is apparent that the invention herein disclosed fulfills the objects above stated, it will be appreciated that numerous embodiments and modifications may be devised by those skilled in the art, and it is intended that the appended claims cover all such modifications and embodiments as fall within the true spirit and scope of the present invention.

For example, other mechanisms for altering the separation gap in a rheometer may also be used to characterize the rheological properties of a flowing system and alter the microstructure of that flowing system. These mechanisms include, but are not limited to, the use of side fed sliding elements such as those found in screen changers, the use of inflatable means, and the use of expansion/contraction devices which operate via thermal, electrical, magnetic, mechanical or other means.

Additionally, wall slip corrections may be employed to characterize wall slip behavior. Alteration of the rheometer surface properties through roughness, grooves and materials of construction may be used to eliminate wall slip from flowing systems which exhibit this property. These can be done through alteration of the surface characteristics of the equipment as well as through other well-known scientific procedures.

What is claimed is:

1. An adjustable gap rheometer for measuring or characterizing a flowing system comprising:
   a first portion:
   a second portion which mates with said first portion to form a separation gap therebetween constructed to guide a flowing system therethrough; and
   means for moving at least a part of said first portion, said second portion, or both relative to one another so as to adjust the size of the separation gap.

2. An adjustable gap rheometer according to claim 1 wherein at least a part of said first portion moves relative to said second portion.

3. The adjustable gap rheometer according to claim 2 wherein said first and second portions mate to form a slit die configuration wherein the separation gap comprises a slit.

4. The adjustable gap rheometer according to claim 3 wherein said slit comprises a rectangular cross-section.

5. The adjustable gap rheometer according to claim 2 wherein said first portion comprises a tapered bushing and said second portion comprises a tapered mandrel formed to fit within said tapered bushing and move laterally thereto.

6. The adjustable gap rheometer according to claim 5 wherein said taper on said tapered bushing is 10° or less.

7. The adjustable gap rheometer according to claim 5 wherein said taper on said tapered mandrel is 10° or less.

8. The adjustable gap rheometer according to claim 5 wherein said tapered mandrel and said tapered bushing are circular in cross-section.

9. The adjustable gap rheometer according to claim 1 wherein at least one of the first or second portions inflates or deflates to adjust the size of the separation gap.

10. The adjustable gap rheometer according to claim 1 wherein at least one part of the first or second portions expands or contracts via thermal, electrical, magnetic or mechanical means to adjust the size of the separation gap.

11. The adjustable gap rheometer according to claim 1 wherein at least one part of one of the first or second portions uses side fed sliding means to adjust the size of the separation gap.

12. The adjustable gap rheometer according to claim 1 further comprising a plurality of shear stress transducers, optical windows, temperature thermocouples and pressure transducers to measure material properties of the flowing system.

13. The adjustable gap rheometer according to claim 1 further comprising heating/cooling circulation channels to control the temperature of the flowing system.

14. The adjustable gap rheometer according to claim 1 further comprising heaters to control the temperature of the flowing system.

15. The adjustable gap rheometer according to claim 1 wherein said means for moving at least part of said first or second portion comprise a stepper motor.

16. The adjustable gap rheometer according to claim 1 further providing means for maintaining a constant volumetric flow rate in the flowing system.

17. An improved method of performing rheological studies comprising:

providing an adjustable gap rheometer comprising a first portion and a second portion which form a separation gap therebetween;

adjusting said separation gap of said adjustable gap rheometer by moving at least a part of said first portion, said second portion or both portions of said adjustable gap rheometer;

moving a flowing system having a constant volumetric flow rate through said separation gap; and measuring properties of the flowing system so as to characterize the flowing system at that predetermined separation gap.

18. The method according to claim 17 further comprising determining the structure of the flowing system by utilizing microstructural characterization techniques including computer aided tomography, magnetic resonance imaging, acoustic emission techniques and infrared imaging.

* * * * *